United States Patent [19]
Lee et al.

[11] Patent Number: 5,889,027
[45] Date of Patent: Mar. 30, 1999

[54] 3(2H)-FURANONE DERIVATIVES

[75] Inventors: Jae-Hyun Lee; Ihl-Young Choi, both of Daejeon; Hyun-Jin Kim, Pusan; Gyung-Ja Choi, Daejeon, all of Rep. of Korea

[73] Assignee: Korea Research Institute of Chemical Technology, Daejeon, Rep. of Korea

[21] Appl. No.: 981,604

[22] PCT Filed: Jun. 30, 1995

[86] PCT No.: PCT/KR95/00083

§ 371 Date: Dec. 29, 1997

§ 102(e) Date: Dec. 29, 1997

[87] PCT Pub. No.: WO97/02263

PCT Pub. Date: Jan. 23, 1997

[30] Foreign Application Priority Data

Jun. 30, 1995 [KR] Rep. of Korea ................. 1994-8090

[51] Int. Cl.$^6$ .......................... A61K 31/44; C07D 407/04
[52] U.S. Cl. ........................................ 514/336; 546/284.4
[58] Field of Search ......................... 514/336; 546/284.4

[56] References Cited

U.S. PATENT DOCUMENTS

| | | | |
|---|---|---|---|
| 4,568,376 | 2/1986 | Ward | 71/88 |
| 4,568,377 | 2/1986 | Ward | 71/88 |
| 4,663,466 | 5/1987 | Pomidor et al. | 549/68 |
| 5,189,035 | 2/1993 | Curtze et al. | 514/231.2 |
| 5,648,486 | 7/1997 | Cai et al. | 544/124 |

*Primary Examiner*—Joseph K. McKane
*Attorney, Agent, or Firm*—Finnegan, Henderson, Farabow, Garrett & Dunner, L.L.P.

[57] ABSTRACT

The present invention relates to 3(2H)-furanone compounds possessing fungicidal activity to plant fungi and a process for preparing them.

5 Claims, No Drawings

3(2H)-FURANONE DERIVATIVES

This application is a 371 of PCT/KR95/00083 filed Jun. 30, 1995.

BACKGROUND OF THE INVENTION

1. Field of the Invention

The present invention relates to novel 3(2H)-furanone derivatives of the following formula (I) useful as fungicides having excellent activities to plant fungi and a process for preparing them.

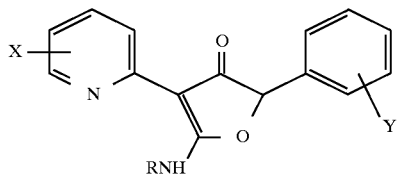

(I)

wherein,
- R is $C_1 \sim C_2$ alkyl, allyl or 2-chloroallyl group;
- X is halogen atom, methyl, $C_1 \sim C_2$ alkoxy, cyano, thioethyl or nitro group; and
- Y is halogen atom, hydrogen, methyl or trifluoromethyl group.

2. Description of the Prior Art

Prior to the present invention, furanone derivatives of the following formula (a) were known as herbicides, but the compounds (a) had not been used as fungicides.

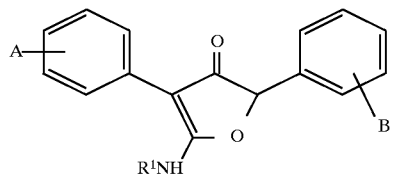

(a)

wherein,
- $R^1$ is alkyl group; and
- A and B are independently halogen atom, trifluoromethyl or alkyl group.

SUMMARY OF THE INVENTION

The object of this invention is to provide novel 3(2H)-furanone compounds of the above formula(I) which have a preventive effect against various kinds of plant fungi, in particular which have selectively excellent fungicidal activities to specific plant fungi.

Another object of this invention is to provide novel fungicidal composition comprising one or more compounds of the above formula(I) as an effective ingredient in combination with an inert carrier.

The present invention relates to 3(2H)-furanone derivatives of the formula(I).

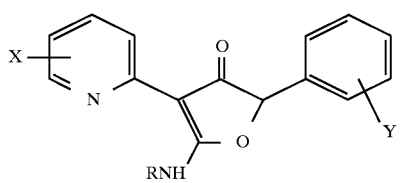

(I)

wherein,
R, X and Y are respectively defined as described previously.

DETAILED DESCRIPTION OF THE INVENTION

According to the present invention, 3(2H)-furanone derivatives of the formula (I) are novel compounds, and have an excellent preventive and fungicidal effect against plant fungi, in particular against rice sheath blight, cucumber gray mold, etc. Therefore, the derivatives are useful as an agricultural and floricultural fungicide ingredient.

In the present invention, 3(2H)-furanone derivatives of the formula(I) may be prepared by the following reaction scheme.

[Reaction Scheme]

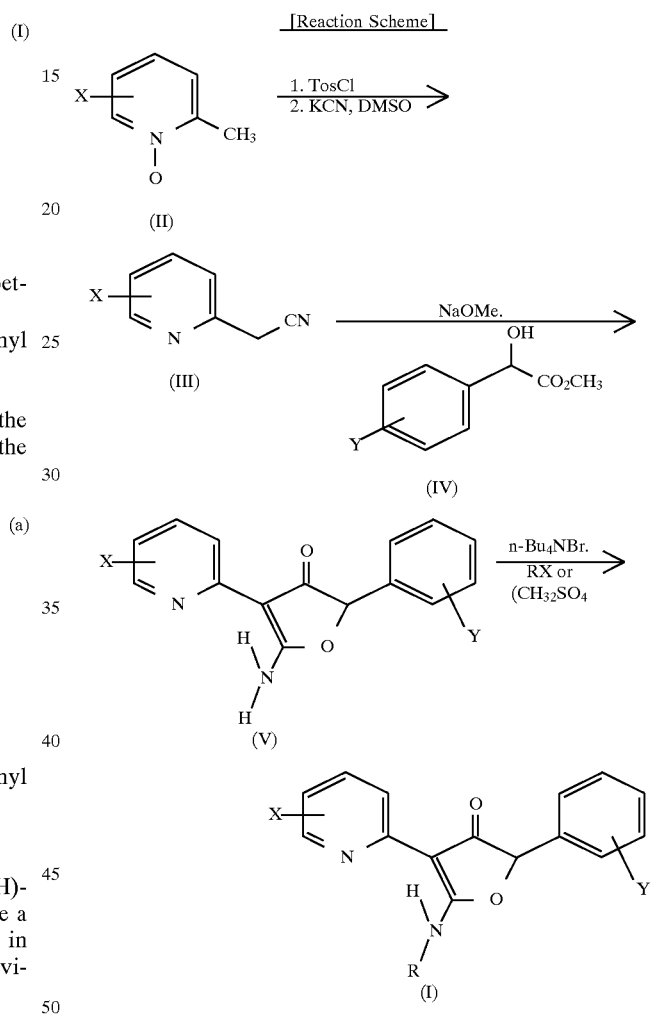

In the above reaction scheme, X, Y and R are respectively defined as described previously.

According to the above reaction scheme, N-oxide compound of the formula(II) prepared by the well-known process is converted into chloropyridine by treating with p-toluenesulfonyl chloride and then it was reacted with potassium cyanide(KCN) in dimethyl sulfoxide(DMSO) to obtain cyanopyridine compound of the formula(III).

The obtained cyanopyridine compound(III) is reacted with hydroxymethylaromatic acid ester compound of the formula(IV) in the presence of a base to prepare aminofuranone of the formula(V). A substituent is introduced at the position of amino group of the formula(V) by reacting with an alkyl or alkenyl halide compound in the presence of a phase transfer catalyst to obtain the desired 3(2H)-furanone derivatives of the formula(I).

According to the present invention, sodium methoxide (NaOMe) may preferably be used as a base, and tetrabutylammonium bromide may preferably be used as a phase transfer catalyst.

In the above formula(I), it may be the preferable compound that X and R are respectively methyl group and Y is chlorine atom.

New compounds of the formula(I) prepared by the present invention may typically be listed in following Table 1.

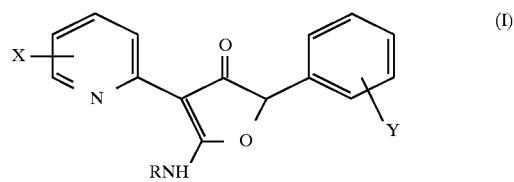

TABLE 1

| Compound No. | X | R | Y | mp(°C.) | ¹H NMR(ppm) |
|---|---|---|---|---|---|
| 1 | 4-CH₃ | CH₃ | H | | 2.37(s, 3H), 3.20(s, 3H), 5.33 (s, 1H), 6.80~8.17(m, 8H), 10.23(s, 1H) |
| 2 | 4-CH₃ | CH₂CH₃ | H | | 1.30(t, 3H), 2.27(s, 3H), 3.55 (q, 2H), 5.43(s, 1H), 6.67~ 8.17(m, 8H), 10.17(s, 1H) |
| 3 | 4-CH₃ | CH₂—CH=CHCl | H | | 2.36(s, 3H), 4.30(q, 2H), 5.90 (s, 1H), 6.13(m, 2H), 6.85~ 8.27(m, 8H), 10.55(s, 1H) |
| 4 | 4-CH₃ | CH₂—CH=CH₂ | H | | 2.27(s, 3H), 4.13(t, 2H), 5.06, 5.23(m, 3H), 5.43(s, 1H), 6.67~8.07(m, 8H), 10.33(s, 1H) |
| 5 | 4-CH₃ | CH₂—CH=CHCl | 4-CH₃ | | 2.34(s, 3H), 2.37(s, 3H), 4.30(m, 2H), 5.53(s, 1H), 6.17(m, 2H), 6.70~8.23(m, 7H), 10.46(s, 1H) |
| 6 | 4-CH₃ | CH₃ | 4-CH₃ | | 2.30(s, 3H), 2.33(s, 3H), 3.17 (s, 3H), 5.53(s, 1H), 6.7~ 8.30(m, 7H), 10.23(s, 1H) |
| 7 | 4-CH₃ | CH₃ | 3-CH₃ | | 2.30(s, 3H), 2.33(s, 3H), 3.17 (s, 3H), 5.43(s, 1H), 6.73~ 8.23(m, 7H), 10.17 (s, 1H) |
| 8 | 4-CH₃ | CH₂—CH=CHCl | 3-CH₃ | | 2.30(s, 3H), 2.33(s, 3H), 4.23 (m, 2H), 5.53(s, 1H), 6.17(m, 2H), 6.77~8.30(m, 7H), 10.80(s, 1H) |
| 9 | 4-CH₃ | CH₃ | 2-F | | 2.36(s, 3H), 3.13(s, 3H), 5.85 (s, 1H), 6.77~8.30(m, 7H), 10.30(s, 1H) |
| 10 | 4-CH₃ | CH₂—CH=CHCl | 2-F | | 2.33(s, 3H), 4.33(m, 2H), 5.80(m, 1H), 6.17(m, 2H), 6.77~8.23(m, 7H), 10.47(s, 1H) |
| 11 | 4-CH₃ | CH₃ | 4-F | | 2.34(s, 3H), 3.15(s, 3H), 5.78 (s, 1H), 6.78~8.43(m, 7H), 10.38(s, 1H) |
| 12 | 4-CH₃ | CH₂CH=CHCl | 3-F | | 2.30(s, 3H), 4.27(m, 2H), 5.47(s, 1H), 6.07(m, 2H), 6.76~8.26(m, 7H), 10.50(s, 1H) |
| 13 | 4-CH₃ | CH₂CH=CHCl | 4-F | | 2.34(s, 3H), 4.22(m, 2H), 5.48(s, 1H), 6.76~8.29(m, 7H), 10.51(s, 1H). |
| 14 | 4-CH₃ | CH₂CH=CHCl | 2-CF₃ | | 2.33(s, 3H), 4.23(m, 2H), 5.97(s, 1H), 6.07(m, 2H), 6.83~8.30(m, 7H), 10.43(s, 1H) |
| 15 | 4-CH₃ | CH₃ | 2-CF₃ | | 2.60(s, 3H), 3.17(s, 3H), 5.97 (s, 1H), 6.93~8.57(m, 7H), 10.33(s, 1H) |
| 16 | 4-CH | CH₃ | 3-CF₃ | | 2.30(s, 3H), 3.20(d, 3H), 5.53 (s, 1H), 6.70~8.30(m, 7H) |
| 17 | 4-CH₃ | CH₂CH=CHCl | 2-Cl | | 2.33(s, 3H), 4.21(m, 2H), 5.50(s, 1H), 6.07(m, 2H), 6.76~8.30(m, 7H), 10.53(s, 1H) |
| 18 | 4-CH | CH₃ | 2-Cl | | 2.37(s, 3H), 3.17(s, 3H), 6.06 (s, 1H), 6.80~8.23(m, 7H), 10.25(s, 1H) |
| 19 | 4-CH₃ | CH₂CH₃ | 2-Cl | | 1.30(t, 3H), 2.30(s, 3H), 3.50 (q, 2H), 6.00(s, 1H), 6.80~ 8.20(m, 7H), 10.27(s, 1H) |

TABLE 1-continued

| Compound No. | X | R | Y | mp(°C.) | $^1$H NMR(ppm) |
|---|---|---|---|---|---|
| 20 | 4-CH$_3$ | CH$_2$CH=CHCl | 2-Cl | | 2.33(s, 3H), 4.30(q, 2H), 5.50 (s, 1H), 6.26(m, 2H), 6.76~8.30(m, 7H), 10.57(s, 1H) |
| 21 | 4-CH$_3$ | CH$_3$ | 4-Cl | | 2.37(s, 3H), 3.23(s, 3H), 5.53 (s, 1H), 6.80~8.30(m, 7H), 10.33(s, 1H) |
| 22 | 4-CH$_3$ | CH$_2$CH=CHCl | 4-Cl | | 2.30(s, 3H), 4.33(m, 2H), 5.50(s, 1H), 6.10(m, 2H), 6.74~8.27(m, 7H), 10.60(s, 1H) |
| 23 | 4-CH$_3$ | CH$_3$ | 2,4-Cl$_2$ | | 2.33(s, 3H), 3.23(s, 3H), 6.00 (s, 1H), 6.76~8.30(m, 7H), 10.33(s, 1H) |
| 24 | 4-CH$_3$ | CH$_2$CH=CHCl | 2,4-Cl$_2$ | | 2.33(s, 3H), 4.30(m, 2H), 5.9 (s, 1H), 6.07(m, 2H), 6.77~8.27(m, 7H) |
| 25 | 4-CH$_3$ | CH$_3$ | 3-Cl | | 2.30(s, 3H), 3.20(s, 3H), 5.47 (s, 1H), 6.80~8.30(m, 7H), 10.30(s, 1H) |
| 26 | 4-Cl | CH$_3$ | 2-Cl | | 3.13(d, 3H), 5.93(s, 1H), 6.84~8.20(m, 7H), 9.76(s, JH) |
| 27 | 4-Cl | CH$_2$CH$_3$ | 2-Cl | | 1.30(t, 3H), 3.50(q, 2H), 5.87 (s, 1H), 6.80~8.37(m, 7H), 9.75(s, 1H) |
| 28 | 4-Cl | CH$_2$CH=CHCl | 2-Cl | | 4.37(t, 2H), 5.93, 6.06(m, 2H), 7.03~8.57(m, 7H), 10.13(s, 1H) |
| 29 | 4-Cl | CH$_3$ | 2-CF$_3$ | | 3.17(d, 3H), 5.97(s, 1H), 6.93~8.27(m, 7H), 10.00(s, H) |
| 30 | 4-Cl | CH$_3$ | 3-CF$_3$ | | 3.17(d, 3H), 5.53(s, 1H), 6.85~8.37(m, 7H), 9.90(s, 1H) |
| 31 | 4-Cl | CH$_3$ | 3-Cl | | 3.27(d, 3H), 5.54(s, 1H), 7.00~8.40(m, 7H), 10.20(s, 1H) |
| 32 | 4-Cl | CH$_3$ | 2,4-Cl$_2$ | | 3.17(d, 3H), 6.00(s, 1H), 6.97~8.53(m, 6H), 9.94(s, 1H) |
| 33 | 4-Cl | CH$_3$ | 4-CH$_3$ | | 2.38(s, 3H), 3.20(d, 3H), 5.47 (s, 1H), 6.90~8.30(m, 7H), 9.87(s, 1H) |
| 34 | 4-Br | CH$_3$ | 2-Cl | | 3.10(d, 3H), 6.00(s, 1H), 6.97~8.47(m, 7H), 10.13(s, 1H) |
| 35 | 4-Br | CH$_2$CH=CHCl | 2-Cl | | 4.33(t, 2H), 5.83, 6.10(m, 2H), 6.10(s, 1H), 6.93~8.47 (m, 7H), 10.13(s, 1H) |
| 36 | 4-Br | CH$_3$ | 3-Cl | | 3.27(s, 3H), 5.60(s, 1H), 7.40~8.47(m, 7H), 10.05(s, 1H) |
| 37 | 4-Br | CH$_3$ | 2,4-Cl$_2$ | | 3.23(s, 3H), 6.03(s, 1H), 7.03~8.47(m, 6H), 10.05(s, 1H) |
| 38 | 4-Br | CH$_3$ | 2-CF$_3$ | | 3.17(d, 3H), 5.93(s, 1H), 6.90~8.50(m, 7H), 9.93(s, 1H) |
| 39 | 4-Br | CH$_3$ | 3-CF$_3$ | | 3.23(d, 3H), 5.57(s, 1H), 6.87~8.40(m, 7H), 10.00(s, 1H) |
| 40 | 4-OCH$_3$ | CH$_3$ | 2-CF$_3$ | | 3.20(s, 3H), 3.87(s, 3H), 6.03 (s, 1H), 6.53~8.28(m, 7H), 10.37(s, 1H) |
| 41 | 4-OCH$_3$ | CH$_3$ | 3-CF$_3$ | | 3.23(d, 3H), 3.85(s, 3H), 5.60 (s, 1H), 6.45~8.23(m, 7H), 10.43(s, 1H) |
| 42 | 4-OCH$_3$ | CH$_3$ | 2-Cl | | 3.17(s, 3H), 3.90(s, 3H), 6.06 (s, 1H), 6.56~8.17(m, 7H), 10.34(s, 1H) |
| 43 | 4-OCH$_3$ | CH$_2$CH=HCl | 2-Cl | | 3.90(s, 3H), 4.30(q, 2H), 6.10 (s, 1H), 6.06, 6.26(m, 2H), 6.60~8.23(m, 7H), 10.07(s, 1H) |
| 44 | 4-OCH$_3$ | CH$_3$ | 3-Cl | | 3.27(s, 3H), 3.90(s, 3H), 5.90 (s, 1H), 6.94~8.23(m, 7H), 10.37(s, 1H) |
| 45 | 4-OCH$_3$ | CH$_2$CH=CHCl | 3-Cl | | 3.87(s, 3H), 4.33(q, 2H), 5.55 (s, 1H), 6.15~6.20(m, 2H), 6.57~8.12(m, 7H), 10.70(s, 1H) |
| 46 | 4-OCH$_3$ | CH$_3$ | 2,4-Cl$_2$ | | 3.24(d, 3H), 3.90(s, 3H), 6.07 (s, 1H), 6.64~8.26(m, 6H), 10.56(s, 1H) |
| 47 | 4-OCH$_3$ | CH$_2$CH=CHCl | 2,4-Cl$_2$ | | 3.90(s, 3H), 4.28(q, 2H), 6.10 (s, 1H), 6.07, 6.28(m, 2H), |

TABLE 1-continued

| Compound No. | X | R | Y | mp(°C.) | ¹H NMR(ppm) |
|---|---|---|---|---|---|
| 48 | 4-OCH$_3$ | CH$_2$CH=CHCl | 3-CF$_3$ | | 6.64~8.25(m, 6H), 10.75(s, 1H) 3.25(s, 3H), 3.90(m, 2H), 5.50(s, 1H), 6.60(m, 2H), 7.25~8.33(m, 7H), 10.44(s, 1H) |
| 49 | 4-OCH$_3$ | CH$_3$ | 3,5-Cl$_2$ | | 3.86(s, 3H), 4.33(s, 3H), 5.57 (s, 1H), 6.10~8.30(m, 6H) |
| 50 | 4-OCH$_3$ | CH$_2$CH=CHCl | 3,5-Cl$_2$ | | 3.28(s, 3H), 3.92(m, 2H), 5.58(s, 1H), 6.20(m, 2H), 6.48~8.28(m, 6H) |
| 51 | 4-NO$_2$ | CH$_3$ | 2-CF$_3$ | | 3.15(d, 3H), 6.00(s, 1H), 6.93~ 8.62(m, 7H), 10.17(s, 1H) |
| 52 | 4-SCH$_2$CH$_3$ | CH$_3$ | 2-CF$_3$ | | 1.40(t, 3H), 3.10(q, 2H), 3.20 (s, 3H), 6.05(s, 1H), 6.83~ 8.55(m, 7H), 10.43(s, 1H) |
| 53 | 4-SCH$_2$CH$_3$ | CH$_3$ | 3,4-Cl$_2$ | | 1.37(t, 3H), 3.06(q, 2H), 3.25 (s, 3H), 5.57(s, 1H), 6.87~ 8.44(m, 6H), 10.40(s, 1H) |
| 54 | 4-SCH$_2$CH$_3$ | CH$_3$ | 3-Cl | | 1.40(t, 3H), 3.07(q, 2H), 3.28 (s, 3H), 5.58(s, 1H), 6.87~ 8.40(m, 7H) |
| 55 | 4-SCH$_2$CH$_3$ | CH$_2$CH=CHCl | 3,4-Cl$_2$ | 138~139 | 1.37(t, 3H), 3.06(q, 2H), 4.38(m, 2H), 5.58(s, 1H), 6.33(m, 2H), 6.82~8.44(m, 6H), 10.60(s, 1H) |
| 56 | 4-SCH$_2$CH$_3$ | CH$_2$CH=CHCl | 3-Cl | | 1.37(t, 3H), 3.07(q, 2H), 4.33(m, 2H), 5.57(s, 1H), 6.33(m, 2H), 6.38~8.40(m, 7H), 10.67(s, 1H) |
| 57 | 4-SCH$_2$CH$_3$ | CH$_3$ | 2,4-Cl$_2$ | | 1.40(t, 3H), 3.17(q, 2H), 3.23(s, 3H), 6.06(s, 1H), 6.73~8.47(m, 6H), 10.40(s, 1H) |
| 58 | 4-SCH$_2$CH$_3$ | CH$_2$CH=CHCl | 2-Cl | | 1.40(t, 3H), 3.13(q, 2H), 4.31(m, 2H), 5.93(s, 1H), 6.40(m, 2H), 6.87~8.56(m, 7H), 10.66(s, 1H) |
| 59 | 4-SCH$_2$CH$_3$ | CH$_3$ | 3-CF$_3$ | | 1.40(t, 3H), 3.13(q, 2H), 3.30(s, 3H), 5.73(s, 1H), 6.93~8.50(m, 7H), 10.47(s, 1H) |
| 60 | 6-CH$_3$ | CH$_2$CH=CHCl | 4-Cl | | 2.47(s, 3H), 4.33(m, 2H), 5.50(s, 1H), 6.15(m, 2H), 6.80~8.27(m, 7H), 10.77(s, 1H) |
| 61 | 6-CH$_3$ | CH$_3$ | 2-CF$_3$ | | 2.63(s, 3H), 3.28(s, 3H), 6.30(s, 1H), 6.90~8.45(m, 7H), 10.40(s, 1H) |
| 62 | 6-CH$_3$ | CH$_3$ | 2-Cl | | 2.50(s, 3H), 3.27(d, 3H), 6.66(s, 1H), 6.77~8.37(m, 7H), 10.33(s, 1H) |
| 63 | 6-CH$_3$ | CH$_2$CH=CHCl | 2-Cl | | 2.43(s, 3H), 4.17(m, 2H), 5.93(s, 1H), 6.10~8.27(m, 7H), 10.60(s, 1H) |
| 64 | 6-CH$_3$ | CH$_3$ | 2,4-Cl$_2$ | | 2.46(s, 3H), 3.13(d, 3H), 5.93 (s, 1H), 6.73~8.30(m, 6H), 10.37(s, 1H) |

The process for preparing the above compound of formula (I) according to the present invention may be further illustrated by the following examples, but the present invention is not limited by the examples.

EXAMPLE 1

2-Cyanomethyl-4-methylpyridine 2,4-Lutidine-1-oxide (10 g, 8.10 mmol) was dissolved in anhydrous dioxane (125 ml) under nitrogen atomsphere, and herein p-toluenesulfonyl chloride (31.5 g, 162 mmol) was added and refluxed for 5 hours. The solution was neutralized with the saturated aqueous solution of potassium carbonate and extracted twice with methylene chloride. The combined organic layers were dried over anhydrous magnesium sulfate, filtered and concentrated under reduced pressure to get crude product. The residue was separated and purified by column-chromatography over silica gel to obtain 2-chloromethyl-4-methylpyridine (4.18 g, yield=36%).

2-chloromethyl-4-methylpyridine (3.70 g, 2.17 mmol) was dissolved in dimethyl sulfoxide (9 ml) and herein potassium cyanide (1.70 g, 2.60 mmol) was added. After stirring for 17 hours at room temperature, water was added and it was extracted twice with diethyl ether. The combined organic layers were dried over anhydrous magnesium sulfate, and concentrated under reduced pressure to get crude product. The residue was separated and purified by column-chromatography over silica gel to obtain the desired product (3.19 g, yield=95%).

EXAMPLE 2

2-(o-Chlorophenyl)-3-oxo-4-(4-methylpyridyl)-5-amino-2,3-dihydrofurane

Sodium (0.35 g, 15.2 mmol) was added in methanol (8 ml) and stirred at room temperature under nitrogen atomsphere till complete dissolution of sodium, and then 2-cyanomethyl-4-methylpyridine (1.10 g, 8.51 mmol) and 2-(o-chlorophenyl)2-hydroxymethylacetic acid (1.78 g, 1.35 mmol) were slowly added. After refluxing for 2 hours with stirring the solution was cooled with a small amount of water and concentrated under the reduced pressure. The residue was extracted with methylene chloride and the combined organic layers were dried over anhydrous magnesium sulfate, filtered and concentrated under reduced pressure to get crude product. The residue was separated and purified by column-chromatography over silica gel to obtain the desired product (0.54 g, yield=28%).

EXAMPLE 3

2-(o-Chlorophenyl)-3-oxo-4-(4-methylpyridyl)-5-methylamino-2,3-dihydrofuran (Compound No. 18)

Solid sodium hydroxide(180 mg, 4.50 mmol) was dissolved in a small amount of water and then added to methylene chloride (8.6 ml) containing 2-(o-chlorophenyl)-3-oxo-4-(4-methylpyridyl)-5-amino-2,3-dihydrofuran(400 mg, 1.3 mmol). Tetrabutylammonium bromide (50.0 mg, 1.37 mmol) was added and then a mixture containing dimethyl sulfate (164 mg, 1.30 mmol) was slowly added at room temperature. The mixture was stirred at room temperature for one hour and then washed twice with water, dried over anhydrous magnesium sulfate. The solvent was evaporated in vacuo to yield a crude product, which was separated by column-chromatography over silica gel to obtain the desired product (370 mg, yield=88%) as a white solid.

Only process for preparing compound No. 18 according to the present invention was written in the above examples, but other compounds according to the present invention may be easily prepared by skilled person in the art.

According to the present invention, 3(2H)-furanone derivative prepared by the above example may be used by itself as agricultural and floricultural fungicide and also prepared as preparation such as powder, wetting powder, emulsifying condensate, granules, pellets, etc. by mixing with common carrier, interfacial active agent, dispersing agent or comaterials.

The fungicidal activities of 3(2H)-furanone derivatives of the formula(I) according to the present invention prepared by the above examples were tested as followings; wherein all of the test chemicals were readily dispersed in a standard formulation of acetone in water and a surfactant. In order to test protective effect against plant fungi for novel compound of the formula(I) according to the present invention 10 ml of acetone containing 25 mg of the compound of formula(I) was diluted in 90 ml of Tween-20 solution producing 250 ppm or 500 ppm solution of the compound of above example. And, 50 ml of this chemical solution was sprayed to the foliages of plants. The sprayed plants were left for 24 hours at room temperature, and solvent and water were sprayed to apply the following test fungi. Two pots of plants were duplicately tested for fungicidal activity, respectively.

TEST 1

Fungicidal Effect on Rice Blast

Fungal isolates of *Pyricularia oryzae* were inoculated on rice polish agar media (20 g rice polish, 10 g dextrose, and 15 g agar in 1 l distilled water) and incubated at 26° C. for 2 weeks. Sporulation was induced in a fluorescent light-illuminated incubator at 25°~28° C. following aerial mycelia were removed from the media by scrapping with a rubber spetular. The spores were harvested with sterile distilled water and adjusted to the concentration of $10^6$ spores/ml. Then the spore suspension was sprayed to rice blast-susceptable rice plants (Nakdong cultivar) which were already treated with test compounds until just before runoff at the stage of 3 or 4 leaves. The inoculated plants were placed in a humidity chamber in darkness at 25° C. for 24 h and transferred to a growth chamber maintained at 26°±2° C. under>90% relative humidity. Five days after the inoculation, disease severity was determined as an area of lesion with the fully expanded leaf which was the second leaf from the top of 3- or 4-leaves plants. The lesion areas were compared with RCB standard rating diagram.

TEST 2

Fungicidal Effect on Rice Sheath Blight

*Rhizoctonia solani* AG-1 were grown in potato dextrose agar media for 3 days and the agar discs were transferred to the Erlnmeyer flask with sterilized wheat bran. After 7 days of incubation, the fungal mycelia were harvested with sterile distilled water and homogenized using Waring blender. The rice plants were inoculated at the stage of 2- or 3- with the homogenates and placed in a humidity chamber in darkness at 28°±1° C. for 48 h. The plants were transferred to a growth chamber maintained at 26°±2° C. under>80% relative humidity. Disease severity was deterermined at 5 days after the inoculation. Lesion areas were expressed as percentages of the lesioned sheath area to the total sheath area. The values for disease severity were obtained from RSB standard rating diagram.

TEST 3

Fungicidal Effect on Cucumber Gray Mold

*Botrytis cinerea* KCl isolated from cucumber were inoculated on PDA media and incubated at 25° C. for 7 days under dark condition. Sporulation was induced in an incubator under 16 h, 25° C. light and 8 h, 20° C. dark conditions for 7 days, the spore harvest was performed as following steps; i.e., addition of 10 ml sterile distilled water into the plate, scrapping the spores with a paintbrush, and filtering the spore suspension through 4 layers of cheesecloth. The concentration of the harvested spore suspension was adjusted to $10^6$ spores/ml. Following the first true leaves of cucumber plants were inoculated with the spore suspension, the plants were placed in a humidity chamber at 20° C. for 5 days. Disease severity on the first ture leaves of plants were evaluated.

TEST 4

Fungicidal Effect on Tomato Late Blight

*Phytophthora infestans* KA2 were inoculated on V-8 juice agar (200 ml V-8 juice, 4.5 g CaCO, 1.5 g agar, 800 ml distilled watr) and incubated under 16/8 light/dark photoperiod conditions at 20° C. for 2 weeks. The sporangia were harvested as same manners in Test 3. The concentration of the harvested spore suspension was adjusted to $10^5$ spores/ml, the sporangium suspension sprayed to the tomato plants at the stage of two true leaves. The plants were placed in a humidity chamber at 20° C. for 4 days under>80% relative humidity. Disease severity on the first and second true leaves of plants were evaluated.

TEST 5

Fungicidal Effect on Wheat Leaf Rust

*Puccinia recondita* were subcultured on wheat plants in a laboratory. For evaluating fungicidal effect, seeds of wheat plants were planted to 6.5 cm-diameter plastic pots. Each pot contained 5 seeds. Seven-day-old plants with one true leaf were applied with the spores. The inoculated plants were incubated in a humidity chamber at 20° C. for 24 h and then transferred to a growth chamber at 20° C. under 70% relative humidity. Disease severity was determined as a percentage of lesion area at 10 days after the inoculation.

TEST 6

Fungicidal Effect on Barley Powdery Mildew

*Erysiphae graminis f. sp. hordei* were subcultured on wheat plants in a laboratory. For evaluating fungicidal effect, seeds of barley plants (Dongboree cultivar) were planted to 6.5 cm-diameter plastic pots. Each pot contained 15 seeds. Seven-day-old plants with one true leaf were applied with the spores. The inoculated plants were incubated in a growth chamber at 22°~24° C. under 50% relative humidity. Disease severity was determined as a percentage of lesion area at 7 days after the inoculation.

Control values for Test 1~6 were calculated with the following equation. The results were presented in Table 2.

$$\text{Control value (\%)} = 1 - \frac{\text{disease severity of treated plants}}{\text{disease severity of untreated plants}} \times 100$$

TABLE 2

| Compound No. | Concentration (ppm) | Control Value (%) RCM[1] | RSB[2] | CGM[3] | TLB[4] | WLR[5] | BPM[6] |
|---|---|---|---|---|---|---|---|
| 15 | 500 | 97 | 100 | 98 | 88 | 67 | 88 |
| 18 | 50 | 96 | 15 | 0 | 0 | 0 | 0 |
| 22 | 500 | 0 | 6 | 92 | 20 | 0 | 20 |
| 23 | 500 | 57 | 38 | 90 | 0 | 0 | 0 |
| 25 | 500 | 0 | 38 | 88 | 37 | 0 | 23 |
| 26 | 500 | 89 | 0 | 99 | 0 | 0 | 4 |
| 26 | 250 | — | — | 97 | — | — | — |
| 29 | 500 | 0 | 20 | 96 | 48 | 0 | 21 |
| 32 | 500 | 0 | 0 | 92 | 13 | 0 | 27 |
| 34 | 500 | 99 | 0 | 92 | 15 | 0 | 36 |
| 34 | 250 | 68 | — | 96 | — | — | — |
| 43 | 500 | 60 | 58 | 96 | 0 | 0 | 4 |
| 44 | 500 | 0 | 30 | 96 | 13 | 14 | 9 |
| 45 | 500 | 0 | 25 | 98 | 0 | 0 | 3 |
| 47 | 500 | 0 | 0 | 88 | 16 | 0 | 30 |
| 53 | 500 | 0 | 11 | 94 | 33 | 0 | 39 |
| 55 | 250 | 0 | 0 | 100 | 3 | 0 | 25 |
| 57 | 500 | 0 | 5 | 94 | 10 | 0 | 31 |
| 61 | 500 | 0 | 21 | 96 | 72 | 0 | 23 |

(1)RCM: Rice Blast
(2)RSB: Rice Sheath Blight
(3)CGM: Cucumber Gray Mold
(4)TLB: Tomato Late Blight
(5)WLR: Wheat Leaf Rust
(6)BPM: Barley Powdery Mildew

What is claimed is:

1. A compound of 3(2H)-furanone having the following formula(I)

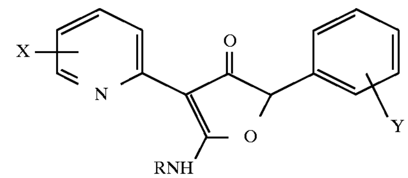

(I)

wherein,

R is $C_1$~$C_2$ alkyl, allyl or 2-chloroallyl group;

X is halogen atom, methyl, $C_1$~$C_2$ alkoxy, cyano, thioethyl or nitro group; and Y is halogen atom, hydrogen, methyl or trifluoromethyl group.

2. The compound of 3(2H)-furanone according to claim 1, wherein R is methyl group, X is methyl group and Y is chlorine atom.

3. A fungicidal composition comprising one or more compounds of formula(I) as an effective ingredient in combination with an inert carrier;

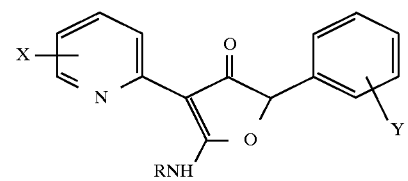

(I)

wherein, R, X and Y are respectively defined as the above claim 1.

4. A process for preparing compounds of formula(I) which comprises the following steps;

reacting N-oxide compound of the following formula(II) with p-toluenesulfonyl chloride and heating the solution;

preparing methylcyanopyridine of the following formula (III) by adding dimethyl sulfoxide and potassium cyanide and reacting at room temperature;

preparing aminofuranone compound of the following formula(V) by reacting hydroxymethylaromatic acid ester compound of the following formula(IV) in the presence of a base catalyst; and introducing a corresponding substituent at the position of amino group of the formula(V) in the presence of a phase transfer catalysts;

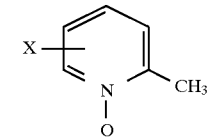
(II)

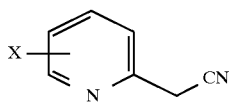
(III)

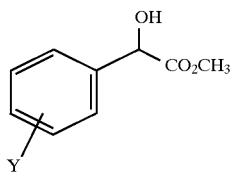
(IV)

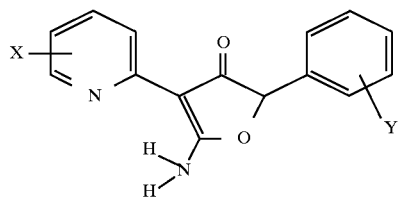
(V)

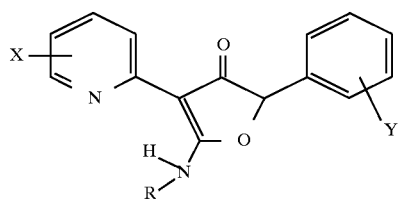
(I)

wherein, R, X and Y are respectively defined as the above claim 1.

5. The process for preparing a compound of 3(2H)-furanone according to claim 4, wherein said base catalyst is sodium methoxide and said phase transition catalyst is tetrabutylammonium bromide.

* * * * *